United States Patent
Gualandi et al.

(10) Patent No.: US 9,408,791 B2
(45) Date of Patent: Aug. 9, 2016

(54) ORAL CARE AND ORAL HYGIENE PRODUCTS HAVING PHOTOCATALYTIC ACTIVITY COMPRISING INORGANIC PARTICLES SUPERFICIALLY FUNCTIONALISED WITH TIO$_2$ NANOPARTICLES

(71) Applicant: Coswell S.p.A, Funo di Argelato (IT)

(72) Inventors: Paolo Gualandi, Funo di Argelato (IT); Andrea Gualandi, Funo di Argelato (IT); Jacopo Gualandi, Funo di Argelato (IT); Michele Gualandi, Funo di Argelato (IT); Marco Lelli, Monghidoro (IT); Marco Marchetti, Montefiore dell'Aso (IT); Filippo Pierini, Bologna (IT); Norberto Roveri, Bologna (IT); Selene Merli, Montecarotto (IT); Giulia Montebugnoli, Monterenzio (IT); Francesca Rinaldi, Ferrara (IT); Eros D'Amen, Bologna (IT)

(73) Assignee: COSWELL S.P.A., Funo di Argelato (BO) (IT)

( * ) Notice: Subject to any disclaimer, the term of this patent is extended or adjusted under 35 U.S.C. 154(b) by 0 days.

(21) Appl. No.: 14/414,624

(22) PCT Filed: Jun. 21, 2013

(86) PCT No.: PCT/IB2013/055116
§ 371 (c)(1),
(2) Date: Jan. 13, 2015

(87) PCT Pub. No.: WO2014/016713
PCT Pub. Date: Jan. 30, 2014

(65) Prior Publication Data
US 2015/0209253 A1    Jul. 30, 2015

(30) Foreign Application Priority Data

Jul. 26, 2012  (IT) .............. MI2012A1310

(51) Int. Cl.
| | | |
|---|---|---|
| *A61K 8/29* | (2006.01) | |
| *A61K 8/24* | (2006.01) | |
| *A61K 8/02* | (2006.01) | |
| *A61C 19/06* | (2006.01) | |
| *A61N 5/06* | (2006.01) | |
| *A61Q 11/00* | (2006.01) | |
| *C09C 1/02* | (2006.01) | |
| *C09C 1/36* | (2006.01) | |
| *B82Y 30/00* | (2011.01) | |
| *B01J 35/00* | (2006.01) | |

(52) U.S. Cl.
CPC ............ *A61K 8/29* (2013.01); *A61C 19/066* (2013.01); *A61K 8/0245* (2013.01); *A61K 8/0254* (2013.01); *A61K 8/24* (2013.01); *A61N 5/062* (2013.01); *A61Q 11/00* (2013.01); *B82Y 30/00* (2013.01); *C09C 1/02* (2013.01); *C09C 1/021* (2013.01); *C09C 1/36* (2013.01); *A61K 2800/413* (2013.01); *A61K 2800/61* (2013.01); *A61K 2800/621* (2013.01); *A61K 2800/651* (2013.01); *A61K 2800/805* (2013.01); *A61K 2800/88* (2013.01); *B01J 35/004* (2013.01); *C01P 2002/72* (2013.01); *C01P 2002/85* (2013.01); *C01P 2004/04* (2013.01); *C01P 2004/54* (2013.01); *C01P 2004/64* (2013.01)

(58) Field of Classification Search
USPC ..................... 510/116, 302; 424/53; 426/3
See application file for complete search history.

(56) References Cited

U.S. PATENT DOCUMENTS

| | | | | |
|---|---|---|---|---|
| 6,825,155 | B2 * | 11/2004 | Nonami et al. ............... | 510/116 |
| 6,843,981 | B1 * | 1/2005 | Ishibashi et al. ............... | 424/53 |
| 2006/0182845 | A1 * | 8/2006 | Grawe et al. ..................... | 426/3 |
| 2006/0240386 | A1 * | 10/2006 | Yaniv et al. ................... | 433/215 |

FOREIGN PATENT DOCUMENTS

| | | | |
|---|---|---|---|
| EP | 1192933 A1 | 4/2002 | |
| JP | 2000327315 A | 11/2000 | |
| JP | 2001-270709 | * 10/2001 | ............. C01B 25/32 |
| WO | WO 2007/137606 A1 | 12/2007 | |

OTHER PUBLICATIONS

Jia et al., "Mesoporous anatase with milti-morphologies synthesized by sol-gel method" Materials and Ltters 60; 1839-1842: 2006.*
E. Landi, A. Tampieri, G. Celotti, S. Sprio, "Densification behaviour and mechanisms of synthetic hydroxyapatites," J. Eur. Ceram. Soc., 2000, 20, 2377-2387.
Harry's Cosmeticology, Seventh Edition, 1982, Edited by J.B. Wilkinson and R.J. Moore.
(Continued)

*Primary Examiner* — Walter Webb
(74) *Attorney, Agent, or Firm* — Husch Blackwell LLP (57) ABSTRACT

The present invention refers to oral care and oral hygiene products having photocatalytic activity comprising particles of a calcium phosphate compound, superficially functionalised with TiO2 nanoparticles in crystalline form, said TiO2 nanoparticles having: a) a substantially lamellar morphology; b) an aspect ratio (AR) comprised between 5 and 30; c) a surface structure having face (001) as outermost face of the crystalline lattice; and d) wherein the TiO2 is in the form of anatase, optionally mixed with rutile and/or brookite.

29 Claims, 5 Drawing Sheets

(56) References Cited

OTHER PUBLICATIONS

Hua Gui Yang et al., "Solvothermal Synthesis and Photoreactivity of Anatase TiO2 Nanosheets with Dominant {001} Facets," J. Am. Chem. Soc. vol. 131, No. 11, 2009, 4078-4083.

S. Ardizzone, C.L. Bianchi, G. Cappelletti, A. Naldoni, C. Pirola; "Photocatalytic Degradation of Toluene in the Gas Phase: Relationship between Surface Species and Catalyst Features," Environ. Sci. Technol. 2008, 42, 6671-6676.

International Search Report and Written Opinion dated Oct. 7, 2014.

* cited by examiner

ORAL CARE AND ORAL HYGIENE PRODUCTS HAVING PHOTOCATALYTIC ACTIVITY COMPRISING INORGANIC PARTICLES SUPERFICIALLY FUNCTIONALISED WITH $TiO_2$ NANOPARTICLES

CROSS REFERENCE TO RELATED APPLICATION

This application is a U.S. National Phase Application of International Application PCT Application No. PCT/IB2013/055116 filed on Jun. 21, 2013, which claims the benefit of priority from Italian Patent Application No. MI2012A001310 filed on Jul. 26, 2012. The disclosures of International Application PCT Application No. PCT/IB2013/055116 and Italian Patent Application No. MI2012A001310 are incorporated herein by reference.

BACKGROUND OF THE INVENTION

The present invention relates to oral care and oral hygiene products comprising inorganic particles superficially functionalised with titanium dioxide ($TiO_2$) and to a process for their preparation.

More specifically, the invention relates to oral care and oral hygiene products comprising particles of a calcium phosphate compound superficially functionalised with $TiO_2$ nanoparticles such as, for example, toothpaste, tooth powder, chewing gum, ointment for the gums, mouthwash and mouth bath concentrate, gargle, bite and mouthguard fillers and whitening professional products.

According to other aspects, the invention relates to the use of the aforementioned oral care and oral hygiene products for preventing and eliminating dental stains (dental dyschromia) and plaque, as well as, to a kit of parts comprising at least one of the aforementioned products and optionally at least a light emitting device having a wavelength comprised between 280 nm and 450 nm (UVB-UVA-Vis).

PRIOR ART

The plaque, more precisely bacterial plaque, is an aggregate (biofilm) of germs tenaciously adherent to each other and to the tooth surfaces, which promotes and supports the common oral diseases: dental caries and periodontal diseases.

The plaque can only be removed by mechanical cleaning. For this reason, the areas where it is deposited more easily are those that run away with self-cleaning and with an approximate oral hygiene. Bonded to the tooth surfaces, the plaque disgregates the enamel acting with its chemical products: lactic acid and pyrophosphatase that attack the hydroxyapatite (the main component of enamel), aminopeptidase that destroys the interprismatic protein component of enamel. Thus, dental caries start, which at first will have a very slow progress and an horizontal expansion higher than vertical, because the enamel is particularly hard. Once the enamel be drilled, bacteria reach the dentin, which is demineralized much more rapidly, until the bacteria reach the tooth pulp causing its inflammation and severe pain. Initially the plaque is whitish, sticky and filamentous. After a short time, for the deposition of calcium salts, it becomes caseous, chalky, until to become tartar, a hard yellowish densification that can not be removed even with the brush but only with ultrasonic or surgical instruments.

Among the compounds of calcium phosphate, the hydroxyapatite ($Ca_{10}(PO_4)_6(OH)_2$) is an ionic compound (HA) having important technological applications. In addition to constituting the inorganic phase of bone and teeth, it is present in nature as mineral both geological and biological and can be synthesized with numerous and various chemical processes. The synthetic hydroxyapatite is a biomaterial with multiple applications in the biomedical field as a bone substitute and drugs distributor, in addition to being well known as the most used material for the chromatographic separation of proteins.

The international patent application WO 2007/137606 discloses carbonate-substituted hydroxyapatite nanoparticles, specifically for locally remineralizing the teeth.

Titanium dioxide ($TiO_2$), characterised by three polymorphs anatase, rutile and brookite of which only the first has photocatalytic activity, is a material that has been studied and used for decades in numerous practical applications. While rutile has been widely used to provide the white colour to paints, plastics, cements and cosmetics, anatase has well-known capabilities as a photocatalyst or photopromoter for degrading organic compounds under UV radiation. The ability to promote such chemical transformations makes them very interesting for applications in the field of environmental pollution to improve the quality of air and water and to make solid surfaces antiseptic. Moreover, it is used in building for preparing mortars and materials in general for external coatings in order to keep clean surfaces (cement, glass and ceramic) from pollutants ("self-cleaning" surfaces), or in viaducts and roadways to reduce the level of nitrogen oxides ($NO_x$) and carbon (particulate) present in the exhaust gases of internal combustion engines.

$TiO_2$ anatase is able to absorb solar energy and make it available to decompose polluting substances through specific radical reactions. This property is due to the fact that Ti is a semi-conductor, i.e. a material with intermediate electrically conducting properties between those typical of a metal (conductor) and an insulator (non-conductor). The atoms that make up a solid are bound together by chemical bonds that involve the bonding electrons. The electrons of the entire material occupy the energy levels, firstly filling the free ones with lowest energy. As the number of atoms making up the material increases, the number of electrons forming the bonds and the number of levels that host them increase. When there are a very large number of levels and they have similar energies, they form continuous bands. The bands are common to all the material and the electrons can move freely in them in the entire solid (delocalised electrons).

If the electron band (known as valence band) is not completely full with electrons, the movement of electrons and therefore conduction is possible. The material thus described is a conductor of electrons.

On the other hand, if the valence band is completely full with electrons, it is not possible to occupy it with other electrons. However, there is another higher energy band, not contiguous with the valence band, known as conduction band. The bands are separated by a well-defined energy (energy gap) and the electrons can be promoted from the valence band to the conduction band if an energy greater than the gap is supplied to the system.

If the gap is too great with respect to the energy supplied, no electron can go beyond it and the material behaves as an insulator. If the gap is not too high, part of the electrons can pass from the valence band to the conduction band, leaving a hole in the former and occupying energy levels in the latter. A material with these properties is a semi-conductor. Promotion is possible provided there is absorption of energy by the electrons, for example in the form of heat energy or, like in the present case, of photons.

Anatase has a gap of about 3 eV, an energy corresponding to radiation in the ultraviolet range (wavelengths lower than 400 nm).

UV radiation promotes an electron in the conduction band and leaves a hole in the valence band. Both the hole and the electron can react in aqueous solution or in air with oxidising or reducing agents present in the environment and produce strongly oxidising radical species.

The latter are in turn able, through complex reactions, of oxidising most of the organic substances, transforming them into $CO_2$ and nitrates, i.e. until they are completely removed.

The photocatalytic action promoted by titanium dioxide anatase can be used to reduce organic substances in general and bacteria through the deterioration of their cellular membrane.

SUMMARY OF THE INVENTION

The Applicant has observed that the titanium dioxide commonly used has the limitation of having to be activated by UV light (wavelengths lower than 400 nm) and therefore it is not suitable for use in ambient light conditions (visible light).

The Applicant has therefore set itself the problem of providing oral care and oral hygiene products having photocatalytic activity that allow to prevent and eliminate dental stains and plaque, even by visible light.

The Applicant has surprisingly and experimentally found that it is possible to obtain a dental stain-resistant ant antiplaque action, long lasting, even in the limited time available during the normal routine of dental hygiene.

More particularly, according to a first aspect, the present invention relates to oral care and oral hygiene products having photocatalytic activity comprising particles of a calcium phosphate compound, superficially functionalised with $TiO_2$ nanoparticles in crystalline form, said $TiO_2$ nanoparticles having:
  a) a substantially lamellar morphology;
  b) an aspect ratio (AR) comprised between 5 and 30;
  c) a surface structure having face (001) as outermost face of the crystalline lattice; and
  d) wherein the $TiO_2$ is in the form of anatase, optionally mixed with rutile and/or brookite.

The Applicant has experimentally found that thanks to the aforementioned specific characteristics of titanium dioxide that will be described further hereafter, it is possible to provide oral care and oral hygiene products having photocatalytic activity that achieve a series of very advantageous technical effects, including the abatement of oral cavity bacteria, by the deterioration of their cellular membrane, which are among the major plaque and dental stains reponsible.

Within the framework of the present description and in the subsequent claims, except where otherwise indicated, all numbers expressing amounts, quantities, percentages, and so forth, are to be understood as being preceded in all instances by the term "about". Also, all ranges of numerical entities include all the possible combinations of the maximum and minimum numerical values and all the possible intermediate ranges therein, in addition to those specifically indicated hereafter.

Within the framework of the present description and in the subsequent claims, the term "particles" is used to indicate nanoparticles or microparticles.

Within the framework of the present description and in the subsequent claims, the term "microparticle" is used to indicate aggregates or "clusters" of the aforementioned inorganic nanoparticles.

In a preferred embodiment of the invention, the particles of the calcium phosphate compound have micrometric dimensions, with a length preferably comprised between 0.2 µm and 10 µm, more preferably comprised between 0.5 µm and 5 µm.

In a preferred embodiment of the invention, the $TiO_2$ nanoparticles have a length lower than 0.1 µm, preferably comprised between 0.01 µm and 0.1 µm.

In a preferred embodiment of the invention, the $TiO_2$ nanoparticles have a thickness comprised between 2 and 5 nm.

In a preferred embodiment of the invention, the $TiO_2$ nanoparticles have a width comprised between 1 and 20 nm.

In a preferred embodiment of the invention, the aforementioned calcium phosphate compound is selected from the group comprising: octacalcium phosphate, tricalcium phosphate, apatite, hydroxyapatite, carbonate hydroxyapatite or the like.

Preferably, the calcium phosphate compound is apatite or hydroxyapatite. In a further preferred embodiment, the hydroxyapatite is a carbonatehydroxyapatite having the following formula:

$$Ca_{10-x}Zn_x(PO_4)_{6-y}(CO_3)_{y+z}(OH)_{2-z}$$

wherein x is a number comprised between 0.0055 and 0.6, y is a number comprised between 0.065 and 0.9 and z is a number comprised between 0 and 0.32.

Within the framework of the present description and in the subsequent claims, the term "superficially functionalised" is used to indicate that the titanium dioxide nanoparticles are bound on the surface of the calcium phosphate compound particles by the formation of strong interactions such as, for example, electrostatic bonds.

The single nanoparticles of the calcium phosphate compound can have different morphologies, but preferably they have a substantially lamellar or needle-shaped morphology.

Advantageously, the substantially lamellar morphology allows to increase the surface area of the nanoparticles and consequently to increase their reactivity. Within the framework of the present description and in the subsequent claims, the term "substantially lamellar morphology", is used to indicate a flat and elongated morphology, for example in the form of a plate.

Within the framework of the present description and in the subsequent claims, the term "aspect ratio (AR)" is used to indicate the length/width ratio of a particle.

Within the framework of the present description and in the subsequent claims, the term "outermost face of the crystalline lattice" is used to indicate the widest flat part corresponding to the face (001) of anatase.

In a preferred embodiment of the invention, the calcium phosphate compound further comprises zinc ions.

Preferably, the degree of zinc ions substitution into the structure of the calcium phosphate compound is comprised in the range from 0.1% to 20% by weight with respect to the total content of calcium.

In another preferred embodiment of the invention, the calcium phosphate compound further comprises carbonate ions.

Preferably, the degree of substitution of the carbonate into the structure of the calcium phosphate compound is comprised within the range from 0.5 to 10% by weight with respect to the total content of phosphate.

Preferably, the particles of the aforementioned calcium phosphate compound have a surface having free positive and/or negative charges in order to have a lack of neutralization between the positive charges (cations) and the negative charges (anions) thus advantageously allowing strong interactions (for example electrostatic bonds) to be formed with the titanium dioxide nanoparticles.

In a preferred embodiment of the invention, the particles of the calcium phosphate compound superficially functionalised with $TiO_2$ nanoparticles have a crystallinity degree (CD) comprised between 50% and 80%, more preferably comprised between 58% and 75%.

For the purposes of the invention, the crystallinity degree (CD) can be measured using methods that are well-known to the man skilled in the art, such as for example by x-ray diffraction analysis.

Within the framework of the present description, the crystallinity degree (CD) is measured according to the method described in Landi, E., Tampieri, A., Celotti, G., Sprio, S., "*Densification behaviour and mechanisms of synthetic hydroxyapatites*", J. Eur. Ceram. Soc., 2000, 20, 2377-2387:

$$CD=(1-X/Y)\cdot 100$$

wherein:

Y=height of the maximum diffraction at 2θ=33°, X=height of the background diffraction at 2θ=33° of the nanoparticles X-ray diffraction pattern.

In a preferred embodiment, the present invention relates to an oral care and oral hygiene product having photocatalytic activity in the form of suspension, oil, gel or solid.

According to a preferred embodiment of the invention, the oral care and oral hygiene product having photocatalytic activity is in the form of a suspension including from 1% to 40% by weight of the particles of the calcium phosphate compound superficially functionalised with $TiO_2$ nanoparticles.

In a preferred embodiment of the invention, the suspension has pH comprised between 6 and 13.

In this way, the suspension may be advantageously directly used as such or mixed with other ingredients in the formulation of effective oral care and oral hygiene products.

Most advantageously, this suspension may be produced by means of a quite simple and economic method, as will be described in more detail hereinbelow, and may be directly used, for example as a gargle or mouthwash, to treat the teeth and gums or may be mixed with other ingredients when formulating a solid or liquid product such as a toothpaste or a mouthwash.

In either case and in a preferred embodiment, it has proved advantageous to add suitable preserving agents, such as parabens or other orally acceptable preservatives known to those in the art, in order to prolong the shelf-life of the suspension and avoid the possibility of mold or bacterial contamination.

The inventors have surprisingly observed that the suspension of the invention is stable for an extended period of time even if no stabilizing agents are added thereto.

In particular, it has been observed that the suspension of the invention is stable for at least 30 days and, more generally, for about two-three months, without using any stabilizing agent.

According to a preferred embodiment of the invention, the oral care and oral hygiene products are selected from the group comprising: toothpaste, tooth powder, chewing gum for oral and dental hygiene, ointment for the gums, mouthwash and mouth bath concentrate and gargle.

According to another preferred embodiment, the oral care and oral hygiene products according to the invention in the form of paste or concentrated gel can be used as bite and mouthguard fillers or can be directly applied on the teeth of a subject who subsequently wearing the bite or mouthguard for a number of hours during the day or throughout the night. In this way, one can advantageously obtain whitening action at home without professional intervention by the dentist.

According to a preferred embodiment, the oral care and oral hygiene products according to the invention can be whitening professional products having whitening action with professional intervention by the dentist.

The oral care and oral hygiene products of this invention will, of course, also preferably contain other ingredients commonly used and known in the art to formulate such products, depending on the form of the oral product.

For instance, in the case of an oral product in the form of a dentifrice cream or paste, the product will preferably comprise a particulate abrasive agent, a humectant-containing liquid phase and a binder or thickener which acts to maintain the abrasive agent in stable suspension in the liquid phase. A surfactant and a flavoring agent are also usual preferred ingredients of commercially acceptable dentifrices.

For the purposes of the invention, a suitable particulate abrasive agent is preferably selected from the group comprising: silica, alumina, hydrated alumina, calcium carbonate, anhydrous dicalcium phosphate, dicalcium phosphate dihydrate and water-insoluble sodium metaphosphate. The amount of particulate abrasive agent will generally range from 0.5% to 40% by weight of the toothpaste. Preferred humectants are glycerol and sorbitol syrup (usually comprising an approximately 70% solution). However, other humectants are known to those in the art including propylene glycol, lactitol, and hydrogenated corn syrup. The amount of humectant will generally range from 10% to 85% by weight of the toothpaste. The liquid phase can be aqueous or nonaqueous.

Likewise, numerous binding or thickening agents have been indicated for use in dentifrices, preferred ones being sodium carboxymethylcellulose and xanthan gum. Others include natural gum binders such as gum tragacanth, gum karaya and gum arabic, alginates and carrageenans. Silica thickening agents include the silica aerogels and various precipitated silicas. Mixtures of binders may be used. The amount of binder included in a dentifrice is generally between 0.1% and 5% by weight.

It is usual and preferred to include a surfactant in a dentifrice and again the literature discloses a wide variety of suitable materials. Surfactants which have found wide use in practice are sodium lauryl sulfate and sodium lauroylsarcosinate. Other anionic surfactants may be used as well as other types such cationic, amphoteric and non-ionic surfactants. Surfactants are usually present in an amount comprised between 0.5% and 5% by weight of the dentifrice.

Flavors of possible use are those usually used in dentifrices, for example those based on oils of spearmint and peppermint. Examples of other flavoring materials which may be used are menthol, clove, wintergreen, eucalyptus and aniseed. An amount comprised between 0.1% and 5% by weight is a suitable amount of flavor to incorporate in a dentifrice.

The oral care and oral hygiene products of the invention may include a wide variety of other optional ingredients.

In the case of an oral product in the form of a toothpaste, these optional ingredients may include an anti-plaque agent such as moss extract, an anti-tartar ingredient, such as a condensed phosphate, e.g. an alkali metal pyrophosphate, hexametaphosphate or polyphosphate; a sweetening agent, such as saccharine and salts thereof; an opacifying agent, such as titanium dioxide; a preservative, such as formalin; a coloring agent; a pH controlling agent, such as an acid, base or buffer, such as citric acid. Suitable amounts of these optional ingredients may be easily selectable by those skilled in the art as a function of the specific characteristics to be imparted to the toothpaste.

In the case of an oral product in the form of a chewing gum, the composition will comprise in addition to the ingredients mentioned above a suitable gum base which may be easily selectable by those skilled in the art.

In the case of an oral product in the form of a mouthwash or gargle, the composition will comprise suitable ingredients in liquid or soluble form easily selectable by those skilled in the art, such as sorbitol, glycerol, oils and flavoring materials, solubilizing agents such as hydrogenated and ethoxylated ricin oil, surfactants, such as sodium lauryl sulfate and sodium lauroylsarcosinate, preserving agents, viscosity regulators and other suitable ingredients which may be easily selectable by those skilled in the art.

For a fuller discussion of the formulation of oral compositions reference is made to Harry's Cosmeticology, Seventh Edition, 1982, Edited by J. B. Wilkinson and R. J. Moore.

According to a second aspect thereof, the present invention relates to compositions having photocatalytic activity comprising the aforementioned particles of a calcium phosphate compound superficially functionalised with $TiO_2$ nanoparticles. According to a third aspect thereof, the present invention relates to the aforementioned particles of a calcium phosphate compound superficially functionalised with $TiO_2$ nanoparticles.

According to a fourth aspect thereof, the present invention relates to a first process for manufacturing an oral care and oral hygiene product having photocatalytic activity selected from the group comprising: toothpaste, tooth powder, chewing gum, ointment for the gums, mouthwash and mouth bath concentrate, gargle, bite and mouthguard fillers and whitening professional products, comprising the steps of:
a) providing an aqueous suspension including particles as herein described; and
b) mixing said aqueous suspension with other ingredients of the oral care and oral hygiene product.

This first process advantageously allows to readily incorporate the particles in the oral care and oral hygiene product in a quite simple and convenient manner exploiting the useful properties, in particular stability and pH characteristics, of the suspension of the aforementioned particles.

According to a fifth aspect thereof, the present invention relates to a second process for manufacturing an oral care and oral hygiene product having photocatalytic activity selected from the group comprising: toothpaste, tooth powder, chewing gum, ointment for the gums, mouthwash and mouth bath concentrate, gargle, bite and mouthguard fillers and whitening professional products, comprising the steps of:
a') providing solid particles as herein described; and
b') mixing the solid particles with other ingredients of the oral care and oral hygiene product.

According to a preferred embodiment of the first process according to the invention, the step a) comprises the steps of:
$a_1$) preparing an aqueous solution comprising calcium ions at a concentration comprised between $10^{-4}M$ and $10^{-2}M$, preferably $10^{-3}M$;
$b_1$) heating said aqueous solution to a temperature comprised between 30° and 120° C., preferably 80° C., for a time comprised between 0.5 and 4 hours until said temperature is reached;
$c_1$) adding drop-wise an aqueous solution containing phosphate ions at a concentration comprised between $0.5\ 10^{-4}M$ and $0.5\ 10^{-2}M$, preferably $0.6\ 10^{-3}M$, over a time ranging between 2 h and 8 h, preferably 4 h;
$d_1$) adding drop-wise, simultaneously with the addition of the solution containing phosphate ions, an alcoholic solution of a titanium compound at a concentration comprised between $0.05\ 10^{-4}M$ and $0.05\ 10^{-2}M$, preferably $0.05\ 10^{-3}M$;

$e_1$) refluxing the resulting mixture for a time comprised between 4 h and 12 h, preferably 8 h.

Preferably, in step $d_1$), the alcohol used to make the alcohol solution is selected from the group comprising: methanol, ethanol, isopropanol, propanol, butanol, octanol and mixtures thereof.

Preferably, in step $d_1$), the titanium compound used is selected from the group comprising: a titanium alkoxide, preferably titanium isopropoxide or titanium butoxide, and an inorganic precursor of titanium dioxide.

Preferably, the aforementioned inorganic precursor of titanium dioxide is selected from titanium oxychloride ($TiOCl_2$), titanium tetrachloride ($TiCl_4$) and mixtures thereof in a suitable aprotic solvent.

Preferably, the aforementioned calcium ions come from the saline hydrolysis of $Ca(OH)_2$, $CaCO_3$, $Ca(NO_3)_2.4H_2O$, $Ca(NO_3)_2.2H_2O$, $Ca(CH_3COO)_2$ or mixtures thereof.

Preferably, the aforementioned aqueous solution of step $a_1$) further comprises zinc ions in the form of an oxide or salt of zinc.

Preferably, the phosphate ions present in the aqueous solution of step $c_1$) come from the saline hydrolysis of $NH_4H_2PO_4$, $K_2HPO_4$, $KH_2PO_4$, $H_3PO_4$ or mixtures thereof.

In a preferred embodiment, the aforementioned aqueous solution of step $c_1$) further comprises carbonate ions.

Preferably, the particles of the calcium phosphate compound superficially functionalised with $TiO_2$ of the invention have a crystallinity degree comprised between 50% and 80%, more preferably comprised between 58% and 75%.

In a preferred embodiment of the process, step $c_1$) is carried out by simultaneously agitating the solution, preferably by means of a mechanical stirrer, in order to capture the $CO_2$ present in the atmosphere and obtain a carbonate substitution in the structure of the calcium phosphate obtained.

In this way, the carbonate substitution may be advantageously carried out by simply agitating the solution or suspension for example by means of a mechanical stirrer.

Preferably, the aqueous solution containing phosphate ions of step $c_1$) further comprises carbonate ions.

In a preferred embodiment of the process, step $c_1$) is carried out by simultaneously adding a first solution containing carbonate ions and a second solution containing phosphate ions.

Advantageously, the aforementioned preparation process allows to obtain particles of a calcium phosphate compound functionalised with titanium dioxide with the characteristics described above.

The Applicant has also surprisingly observed that by optimising specific parameters of the synthetic process (for example temperature, mechanical stirring speed, mixing speed of the reactants etc.) it is possible to obtain self assembling of the calcium phosphate nanocrystals in micrometric aggregates that spontaneously tend to neutralize themselves at the surface by covering themselves with nanometric nanocrystals of anatase having dimensions much smaller than those of the calcium phosphate nanocrystals. The self assembling of the calcium phosphate nanocrystals is produced spontaneously through the effect of an amorphous layer on the surface of the crystals wherein the stechiometric Ca/P ratio is not respected and both positive and negative charges are free to neutralize each other. For this reason the self assembling between the calcium phosphate nanocrystals is faster and precedes the subsequent interaction with the anatase nanocrystals that, however, still find free charges to neutralize on the surface of the clusters of calcium phosphate and that expose the widest flat part corresponding to the face (001) of anatase, which is the most reactive face, since it is the least stable (Hua Gui Yang et al. *Solvothermal Synthesis and Pho-* toreactivity of Anatase $TiO_2$ Nanosheets with Dominant {001} Facets J. AM. CHEM. SOC. VOL. 131, No. 11, 2009).

According to a preferred embodiment of the second process according to the invention, the step a') comprises the steps of:

$a_3$) preparing an aqueous suspension including the particles according to step a);

$b_3$) separating the solid particles from the suspension obtained from step $a_3$);

$c_3$) drying the wet solid particles thus obtained.

In a preferred embodiment, the separation step $b_3$) is carried out by decantation, centrifugation or filtration using apparatuses and techniques well known to those skilled in the art.

In a preferred embodiment, the drying step $c_3$) is carried out by freezing the wet solid particles at a temperature lower than 0° C. until reaching a constant weight. Within the framework of this preferred embodiment, the drying step $c_3$) is preferably carried out by freeze-drying the wet solid particles at a temperature comprised between −20° and −50° C., most preferably at about −40° C.

In a preferred embodiment, the process may also comprise the additional step $d_3$) of washing the separated solid particles with water or a basic solution prior to effecting the drying step $c_3$).

Advantageously, this additional washing step $d_3$) serves the useful function of removing any acid residues possibly absorbed or trapped by the particles.

In a preferred embodiment of the processes according to the invention, the mixing step b) and b') is carried out in a mixing apparatus maintained under a predetermined vacuum degree, easily selectable by those skilled in the art in order to obtain a uniform mixture of ingredients, reached by using conventional vacuum pumps.

In another preferred embodiment of the first process according to the invention, the mixing step b) is carried out by $b^1$) mixing the aqueous suspension of step a) with other ingredients of the oral care and oral hygiene product except for any surfactant;

$b^2$) incorporating at least one surfactant into the mixture thus obtained.

In this way, the formation of foam during the mixing operation may be minimized. Within the framework of this embodiment, the incorporation step $b^2$) is preferably carried out under vacuum using a conventional equipment in order to minimize the undesired formation of foam.

According to a sixth aspect thereof, the present invention relates to the use of the oral care and oral hygiene product having photocatalytic activity as herein described, for preventing and eliminating dental stains and plaque.

According to a seventh aspect thereof, the present invention relates to a kit of parts comprising at least an oral care and oral hygiene product having photocatalytic activity according to the invention and optionally at least a light emitting device having a wavelength comprised between 280 nm and 450 nm UVB-UVA-Vis.

Advantageously, the optional use of the aforementioned light emitting device allows an accelerated photoactivation in a shorter time.

Advantageously, the compositions and products having photocatalytic activity according to the invention allow to carry out an antibacterial and anti-plaque effect, with a longer-lasting action, through a suitable activation by UVA light (about 380 nm) and visible light up to 450 nm (blue). Advantageously, therefore, minimal exposure to sunlight is enough to obtain the aforementioned properties and activate the compositions and products according to the invention.

The measurement of the band-gap takes place through the measurement of the diffuse reflectance spectrum. Such measurement carried out directly on the powdered material has been obtained with a UV-VIS Spectrophotometer equipped with a Praying Mantis diffuse reflectance accessory and sampling kit (Harrick Scientific Products). A "total white" material was used as reference. The value of the band-gap of the sample was determined by the Kubelka-Munk equation for diffuse reflectance spectra according to the method described in: S. Ardizzone; C. L. Bianchi; G. Cappelletti; A. Naldoni; C. Pirola. Environ. Sci. Technol. 2008, 42, 6671-6676.

The Applicant has surprisingly and experimentally found that it is possible to achieve the activation of particles having photocatalytic activity according to the invention through radiation with a wavelength up to 450 nm (visible), where sunlight has the maximum intensity.

Advantageously, the products having photocatalytic activity according to the invention allow to carry out, once activated by the appropriate wavelenght (UVA-UVB-VIS), an antibacterial activity in the oral cavity and a whitening activity on the tooth surface.

BRIEF DESCRIPTION OF THE FIGURES

Additional features and advantages of the invention will become more clearly apparent by the following description of some preferred embodiments thereof, given hereinbelow by way of illustration and not of limitation, with reference to the attached drawings. In such drawings.

DETAILED DESCRIPTION OF THE CURRENTLY PREFERRED EMBODIMENTS

Figure 1:
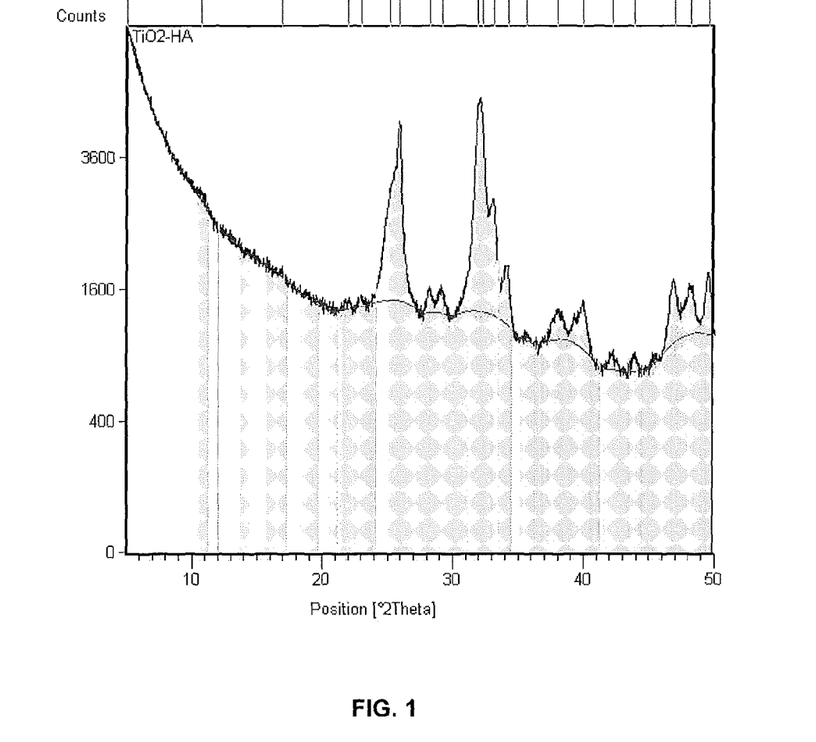
FIG. 1 is an X-ray diffraction spectrum of an example of micrometric particles of hydroxyapatite superficially functionalised with $TiO_2$ (Ex. 1) used for the production of oral care and oral hygiene products having photocatalytic activity according to one aspect of the invention.

With reference to FIG. 1, the X-ray diffraction spectrum shows a crystalline material that has the maximum diffractions characteristic of hydroxyapatite and of anatase.

The maximum diffraction of hydroxyapatite (002) at 25.7 of 2θ partially overlaps the maximum diffraction (100) of anatase at 25.3 of 2θ. The three maximum diffractions in the range 30-35 of 2θ characteristic of hydroxyapatite show how the apatite phase has a low crystallinity degree.

Figure 2:
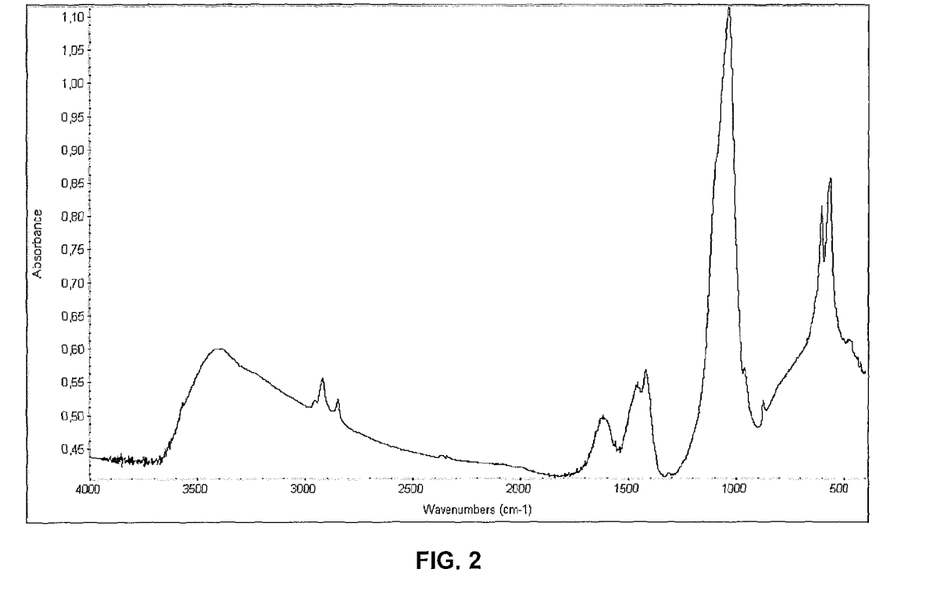
FIG. 2 is a FT-IR spectrum of an example of micrometric particles of hydroxyapatite superficially functionalised with $TiO_2$ (Ex. 1) used for the production of oral care and oral hygiene products having photocatalytic activity according to one aspect of the invention.

With reference to FIG. 2, the FT-IR spectrum of the micrometric particles of example 1 reveals the characteristic absorption bands of hydroxyapatite and of anatase.

As a matter of fact, it is possible to see the band at 435 cm$^{-1}$ characteristic of stretching vTi-O-Ti, the band at 1639 cm$^{-1}$ characteristic of carbonatehydroxyapatite, the bands at 1093 and 1025 cm$^{-1}$ relative to the stretching of the apatite phosphates and the bands at 602 and 565 cm$^{-1}$ relative to the bending of the O—H and O—P—O bonds. It is also possible to see 2 bands at 2906 and 2855 cm$^{-1}$ attributable to the stretching motion vCH2,CH3 of the isopropyl group due to a residue of isopropyl alcohol used in synthesis.

Figure 3:
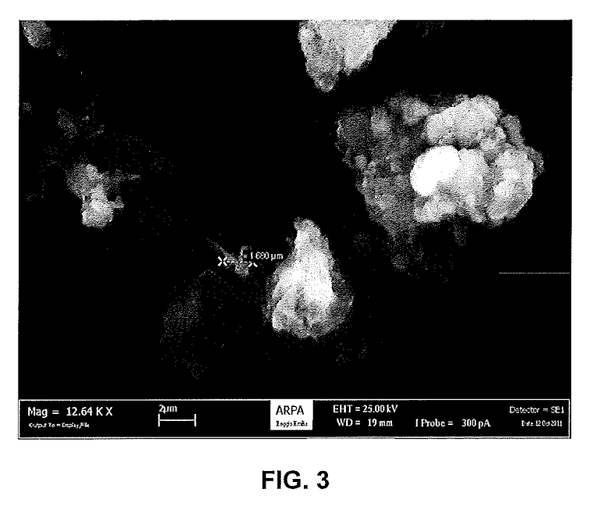
FIG. 3 is a Scanning Electron Microscope (SEM) image of an example of micrometric particles of hydroxyapatite superficially functionalised with $TiO_2$ (Ex. 1) used for the production of oral care and oral hygiene products having photocatalytic activity according to one aspect of the invention.

More particularly and as illustrated in FIG. 3, the Scanning Electron Microscope (SEM) morphological analysis shows that the particles according to one aspect of the invention have crystalline formations of variable dimensions comprised between 0.01 μm and 0.1 μm, the composition of which was determined with elemental microanalysis.

Figure 4:
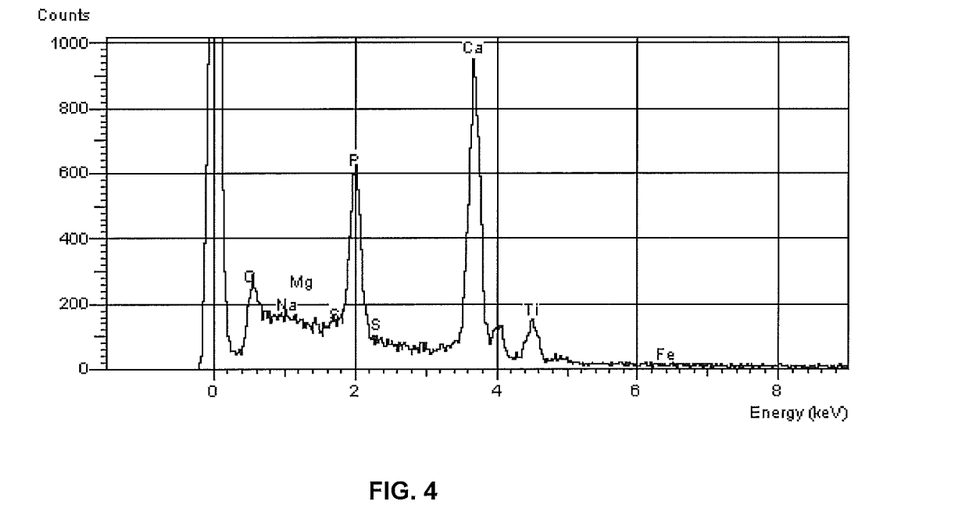
FIG. 4 is an energy dispersion spectrum (EDS) of an example of micrometric particles of hydroxyapatite superficially functionalised with $TiO_2$ (Ex. 1) used for the production of oral care and oral hygiene products having photocatalytic activity according to one aspect of the invention.

With reference to FIG. 4, the spectrum obtained with EDS microanalysis shows that the elemental composition of the aggregates of particles of example 1 consisting of calcium and phosphor in a variable ratio between 1.5 and 1.7, on average 1.6, compatible with that of a non-stechiometric hydroxyapatite. The signal of titanium and that of oxygen are clear. The titanium-oxygen ratio of 1 to 2 was obtained after subtraction of the relative amount of oxygen present in a reference sample of hydroxyapatite. The EDS investigation indicates that a titanium dioxide-hydroxyapatite (TiO$_2$-HA) aggregate was formed since all of the aggregates, analyzed at different points, reveal the same composition and approximately the same composition ratios of calcium, phosphor, titanium and oxygen.

Figure 5:
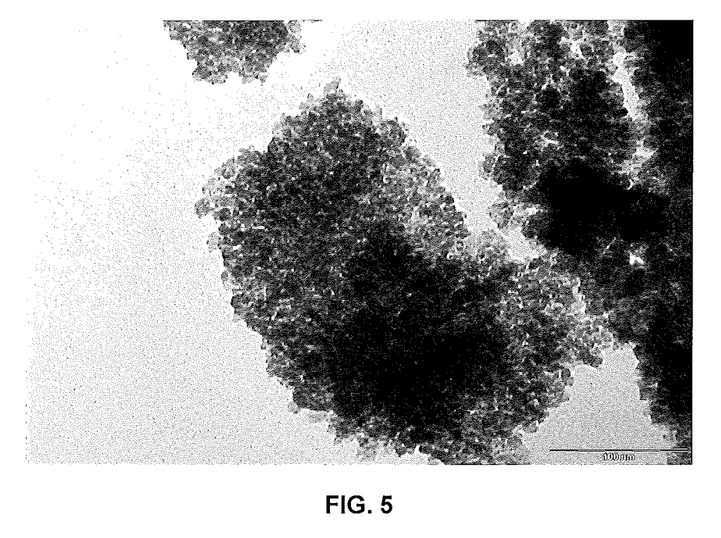
FIG. 5 is a Transmission Electron Microscope (TEM) image of an example of micrometric particles of hydroxyapatite superficially functionalised with $TiO_2$ (Ex. 1) used for the production of oral care and oral hygiene products having photocatalytic activity according to one aspect of the invention.

More particularly and as illustrated in FIG. 5, the Transmission Electron Microscope (TEM) analysis shows that the particles according to one aspect of the invention are in the form of crystalline aggregates with dimensions comprised between 200 and 400 nm.

In the following examples, given purely for indicating and not limiting purposes, the results of a series of experimental tests carried out by the Applicant on the oral care and oral hygiene products according to the present invention will be provided.

EXAMPLE 1

In a reaction ball in a thermostated environment, at a constant temperature of 70° C., 100 mL of a solution containing calcium ions at a concentration equal to 3.60 (of precursor) g/liter were introduced.

Separately 20 mL of a solution containing phosphate ions at a concentration equal to 17.85 g/liter and 40 mL of a solution containing a precursor of titanium and an alcohol at a concentration equal to 20 mmol were prepared.

The two solutions containing the precursor of titanium and the phosphate ions thus obtained were simultaneously introduced inside two droplet-forming apparatuses and then were added to the reaction ball, already containing the calcium ions, under vigorous stirring, at a speed equal to 0.7 ml/min.

After the end of this step, the synthesis product was left to mature inside the reaction environment, keeping it under stirring, in a thermostated environment, for a total time equal to 6.5 hours.

The obtained suspension of carbonate hydroxyapatite particles, superficially functionalised with TiO$_2$ nanoparticles, was thus used for the production of oral care and oral hygiene products having photocatalytic activity according to the invention.

EXAMPLE 2

In a reaction ball in a thermostated environment, at a constant temperature of 80° C., 200 mL of a solution containing calcium ions at a concentration equal to 3.50 (of precursor) g/liter were introduced.

Separately 20 mL of a solution containing phosphate ions at a concentration equal to 16.58 g/liter and 38 mL of a solution containing a precursor of titanium and an alcohol at a concentration equal to 21 mmol were prepared.

The two solutions containing the precursor of titanium and the phosphate ions thus obtained were simultaneously introduced inside two droplet-forming apparatuses and then were added to the reaction ball, already containing the calcium ions, under vigorous stirring, at a speed equal to 0.5 ml/min.

After the end of this step, the synthesis product was left to mature inside the reaction environment, keeping it under stirring, in a thermostated environment, for a total time equal to 9 hours.

The obtained suspension of carbonate hydroxyapatite particles, superficially functionalised with TiO$_2$ nanoparticles, was thus used for the production of oral care and oral hygiene products having photocatalytic activity according to the invention.

EXAMPLE 3

In a reaction ball in a thermostated environment, at a constant temperature of 60° C., 100 mL of a solution containing calcium ions at a concentration equal to 3 (of precursor) g/liter were introduced.

Separately 20 mL of a solution containing phosphate ions at a concentration equal to 14.83 g/liter and 40 mL of a solution containing a precursor of titanium and an alcohol at a concentration equal to 16.67 mmol were prepared.

The two solutions containing the precursor of titanium and the phosphate ions thus obtained were simultaneously introduced inside two droplet-forming apparatuses and then were added to the reaction ball, already containing the calcium ions, under vigorous stirring, at a speed equal to 0.4 ml/min.

After the end of this step, the synthesis product was left to mature inside the reaction environment, keeping it under stirring, in a thermostated environment, for a total time equal to 5.5 hours.

The obtained suspension of carbonate hydroxyapatite particles, superficially functionalised with TiO$_2$ nanoparticles, was thus used for the production of oral care and oral hygiene products having photocatalytic activity according to the invention.

EXAMPLE 4

Evaluation of the Anti-Bacterial activity of an Example 1 Sample

The tests carried out to evaluate anti-bacterial activity were carried out in suspension using the bacterial strain of *Escherichia Coli* ATCC 8739.

The bacterial strains were grown overnight in TSA (Tryptic Soybean Agar) medium. Aliquots of these cultures were inoculated in growing medium (Tryptic Soy Broth) and incubated in aerobic conditions at 37° C. until the exponential growth phase was reached. From these the standard suspensions were then obtained through serial dilutions.

In order to measure the antimicrobial activity, we proceeded by mixing together 2 ml or 4 ml of a sample of example 1 ($TiO_2$-HA) in suspension with the culture medium. Each sample-plate was then inoculated with 2 ml of bacterial suspension at a known level and placed under a UVA lamp for a time of 2 hours at a distance of 8-9 cm from the lamp.

After irradiation, a suitably diluted aliquot (1 ml) taken from each sample and then seeded in plates with agar-rich medium to determine the number of live bacteria present (counted as colony forming units, cfu/ml). The inoculated plates were then placed in incubation at 37° C. for 24 h and the bacterial colonies were then counted.

The results were expressed as survival percentage: $S/S_0$ (inhibition percentage: $1-S/S_0$).

In the following Table 1 the advantages of using the micrometric particles of hydroxyapatite functionalized with $TiO_2$ according to the invention are clear; as a matter of fact, the anti-microbial reduction is 78% after 2 hours of exposure to a UVA lamp, reaching 99.7% by doubling the concentration of the sample according to the invention.

TABLE 1

(Evaluation of anti-bacterial activity on an *Escherichia Coli* strain)

MICROBIAL STRAIN: *Escherichia coli*

| PRODUCT UNDER EXAMINATION | INITIAL MICROBE CONCENTRATION $T_0$ (UFC/ml) | | FINAL MICROBE CONCENTRATION (UFC/ml) | REDUCTION % |
|---|---|---|---|---|
| Deionized sterile water | $1 \times 10^8$ | UVA 2 h | $1 \times 10^8$ | — |
| $TiO_2$-HA (2 ml) | $1 \times 10^8$ | DARK | $9 \times 10^7$ | 8% |
| $TiO_2$-HA (2 ml) | $1 \times 10^8$ | UVA 2 h | $2.1 \times 10^7$ | 78% |
| $TiO_2$-HA (4 ml) | $1.2 \times 10^8$ | UVA 2 h | $2.4 \times 10^6$ | 99.7% |

EXAMPLE 5

Toothpaste

A toothpaste according to the invention was prepared according to the following method and from the following ingredients.

In a first step, an aqueous suspension including carbonate hydroxyapatite particles superficially functionalised with $TiO_2$ nanoparticles ($TiO_2$-HA) (total solid content: 30% by weight) was prepared according to Example 1.

The aqueous suspension thus obtained, was then mixed with the other ingredients of the toothpaste as shown in the table below except for the surfactant.

The mixing was carried out in a conventional mixing apparatus maintained under a suitable vacuum degree selected among the usual values known to those skilled in the art.

Once a homogeneous mixture was obtained, the surfactant was incorporated in the mixing apparatus while maintaining a predetermined vacuum degree.

In this way, a toothpaste was obtained having the composition reported in the following Table 2.

TABLE 2

| Ingredient | Amount [%] |
|---|---|
| Sodium carboxymethylcellulose | 1.0 |
| $TiO_2$-HA particles | 15.0 |
| Sorbitol syrup | 15.0 |
| Glycerine | 15.0 |
| Sodium saccharine | 0.25 |
| Hydroglycolic moss extract titrated in 2% usnic acid | 0.5 |
| Thickening silica | 1.0 |
| Abrasive silica | 18.0 |
| Tetrapotassium pyrophosphate | 3.0 |
| Titanium dioxide | 0.9 |
| Sodium lauryl sulfate | 0.5 |
| Mint flavor | 1.3 |
| Citric acid | 0.25 |
| Water | balance |

EXAMPLE 6

Evaluation of the Coating Formation on the Surface of the Enamel In Vitro

Slabs of enamel (3×3 mm) were obtained from interproximal surfaces of premolars extracted for orthodontic reasons. After the extraction, the teeth were cut with diamond disks and the slabs obtained were sonicated for 10 min in 50% by weight of ethanol in order to removed any debris. The slabs were etched with 37% by weight of orthophosphoric acid for 1 min, then repeatedly washed with distilled water using an electric toothbrush and air dried. The test was then carried out by treating various slabs of enamel with a common toothpaste and an toothpaste containing 10% wt of the $TiO_2$-HA particles according to the present invention.

There have been five tests in parallel for greater repetition of the experiment and better statistical data.

The protocol used was as follows:

Each enamel slab was brushed three times a day for a period of 21 days. The intervals between brushing sessions were more than 5 hours. Any washing process has been performed for 30 sec using an electric toothbrush submitted at constant pressure and using a bean sized aliquot of toothpaste wetted with tap water, closely resembling the in vivo usual tooth-brushing procedure. After every treatment, the single enamel slab was washed with tap water using a cleaned toothbrush in order to remove residual tooth-paste. Toothbrushes were repeatedly washed with tap water after every utilization.

Figure 7A:
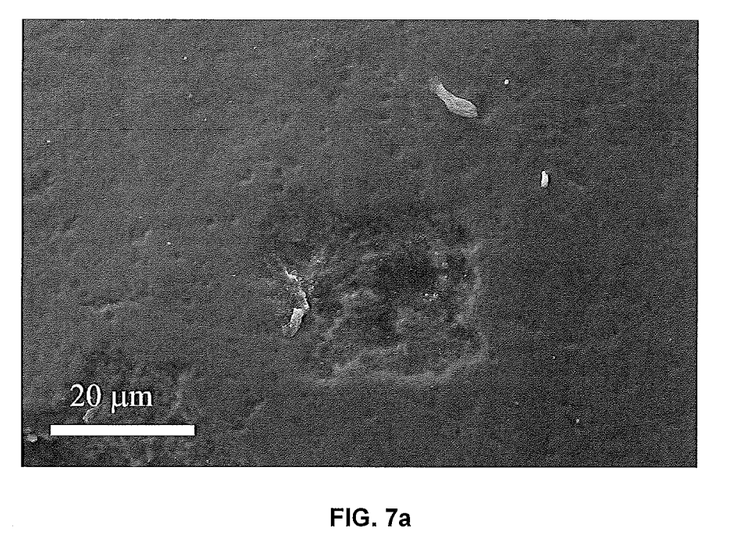
FIG. 7a shows a SEM image and FIG. 7b shows an EDX spectrum of enamel brushed with a common toothpaste.
Figure 7B:
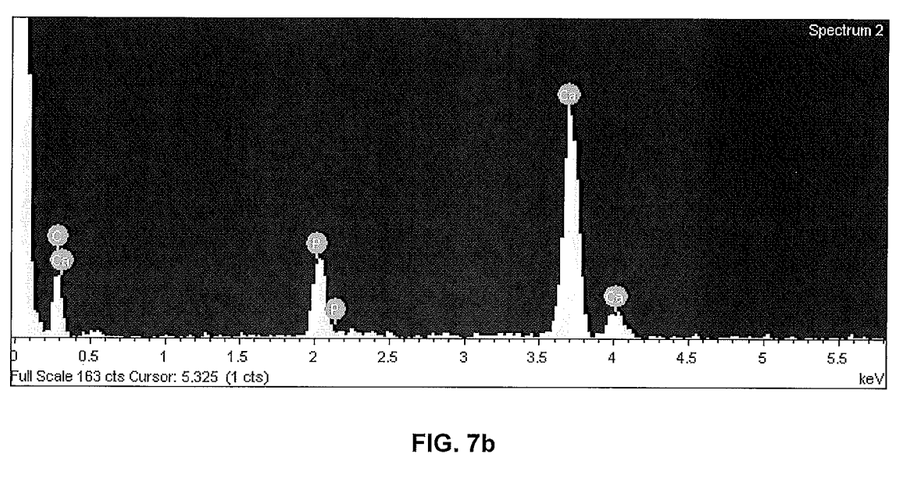

After the brushing treatment 21 days long, each enamel slab have been characterized by X-Ray diffraction technique (DRX), Scanning Electro microscopy (SEM) with EDX probe and Infrared Fourier Transformed Spectroscopy (FTIR). The analysis made by SEM-EDX probe of FIGS. 7*a* and 7*b* show that the enamel surfaces treated with common toothpaste have a Ca/P molar ratio of 1.9 which is the characteristic value of natural enamel.

With EDX probe (FIG. 6*b*), the Applicant shows that the ratio of Ca/P present in the coating is the characteristic value of the calcium phosphate particles superficially functionalised with $TiO_2$ nanoparticles and not the value of natural enamel.

Figure 6A:
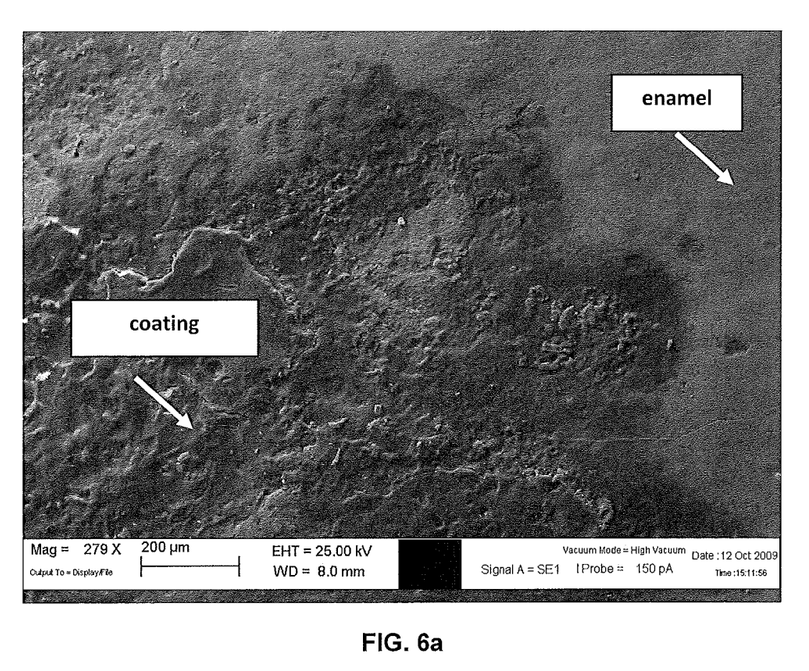
FIG. 6a shows a Scanning Electro microscopy (SEM) image and FIG. 6b shows an Energy Dispersive X-ray (EDX) spectrum of enamel brushed with a toothpaste according to the invention (in vitro test).
Figure 6B:
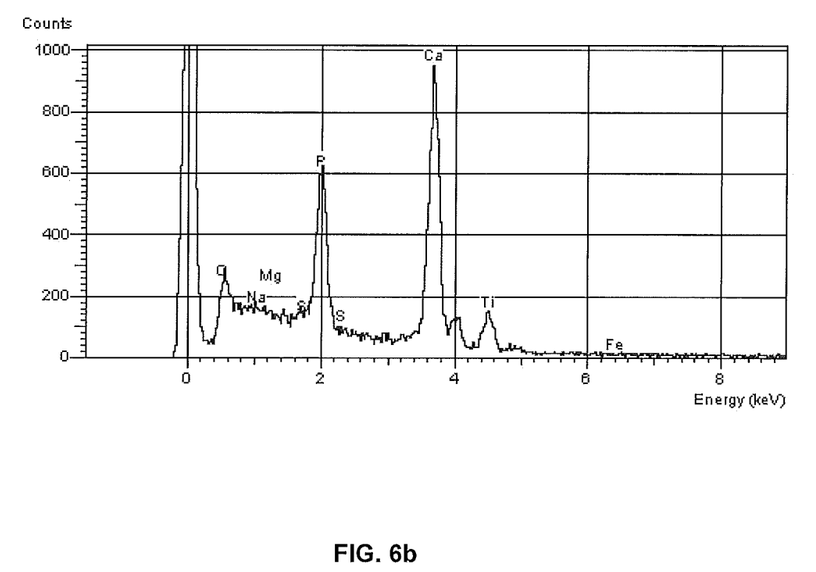

Moreover, it also clearly recognized the signal peak of titanium, characteristic of dioxide.

Thus, on the enamel outer surface treated with a toothpaste according to the invention, a coating be advantageously formed, even in the limited time available during the normal routine of dental hygiene.

EXAMPLE 7

Mouthwash

A mouthwash including TiO$_2$-HA particles according to the invention was prepared by mixing a suspension produced in accordance with the Example 1 in a conventional way with conventional ingredients.

A mouthwash was obtained having the composition reported in the following Table 3.

TABLE 3

| Ingredient | Amount [%] |
|---|---|
| TiO$_2$-HA particles | 5 |
| Sorbitol syrup | 3 |
| Glycerine | 3 |
| Sodium saccharine | 0.25 |
| Hydroglycolic moss extract titrated in 2% usnic acid | 0.5 |
| Tetrapotassium pyrophosphate | 1 |
| Sodium lauryl sulfate | 0.2 |
| Mint flavor | 0.5 |
| Citric acid | 0.1 |
| Water | balance |

EXAMPLE 8

Chewing Gum

A chewing gum including TiO$_2$-HA particles according to the invention was prepared by mixing a suspension produced in accordance with the Example 1 in a conventional way with conventional ingredients.

A chewing gum was obtained having the composition reported in the following Table 4.

TABLE 4

| Ingredient | Amount [%] |
|---|---|
| Chewing gum base | 91.65 |
| TiO$_2$-HA particles | 4 |
| Glycerine | 3 |
| Sodium saccharine | 0.025 |
| Hydroglycolic moss extract titrated in 2% usnic acid | 0.1 |
| Mint flavor | 1 |

Clearly, those skilled in the art may introduce variants and modifications to the above described invention, in order to satisfy specific and contingent requirements, variants and modifications which fall anyhow within the scope of protection as is defined by the following claims.

The invention claimed is:

1. An oral care and oral hygiene product having photocatalytic activity comprising particles of a calcium phosphate compound, superficially functionalised with TiO$_2$ nanoparticles having a dimension smaller than those of the particles of the calcium phosphate compound, the TiO$_2$ nanoparticles being in crystalline form and having:
   a) a substantially lamellar morphology;
   b) an aspect ratio comprised between 5 and 30;
   c) a surface structure having face (001) as outermost face of the crystalline lattice;
   d) wherein the TiO$_2$ is in the form of anatase, optionally mixed with rutile and/or brookite; and
   wherein the TiO$_2$ nanoparticles are linked to the particles of the calcium phosphate compound by means of an electrostatic interaction such that the face (001) of the crystalline lattice of the TiO$_2$ nanoparticles is exposed on the surface of the superficially functionalised particles of the calcium phosphate compound.

2. A product according to claim 1, wherein the particles of the calcium phosphate compound have micrometric dimensions, with a length preferably comprised between 0.2 μm and 10 μm.

3. A product according to claim 1, wherein the TiO$_2$ nanoparticles have a length lower than 0.1 μm.

4. A product according to claim 1, wherein the TiO$_2$ nanoparticles have a thickness comprised between 2 nm and 5 nm.

5. A product according to claim 1, wherein the calcium phosphate compound is selected from the group comprising: octacalcium phosphate, tricalcium phosphate, apatite, hydroxyapatite and carbonate hydroxyapatite.

6. A product according to claim 1, wherein the calcium phosphate compound further comprises zinc ions and/or carbonate ions.

7. A product according to claim 1, wherein the particles of the calcium phosphate compound have a surface having free positive and/or negative charges.

8. A product according to claim 1, wherein the particles of the calcium phosphate compound superficially functionalised with TiO$_2$ nanoparticles have a crystallinity degree comprised between 50% and 80%, preferably comprised between 58% and 75%.

9. A product according to claim 1, in the form of suspension oil, gel or solid.

10. A product according to claim 9, in the form of a suspension including from 1% to 40% by weight of said particles.

11. A product according to claim 10, having a pH comprised between 6 and 13.

12. A product according to claim 9, selected from the group comprising:
   toothpaste, tooth powder, chewing gum for oral and dental hygiene, ointment for the gums, mouthwash and mouth bath concentrate, gargle, bite and mouthguard fillers and whitening professional products.

13. A composition having photocatalytic activity comprising particles of a calcium phosphate compound superficially functionalised with TiO$_2$ nanoparticles according to claim 1.

14. Particles of a calcium phosphate compound superficially functionalised with TiO$_2$ nanoparticles according to claim 1.

15. A process for manufacturing an oral care and oral hygiene product having photocatalytic activity selected from the group comprising: toothpaste, tooth powder, chewing gum, ointment for the gums, mouthwash and mouth bath concentrate, gargle, bite and mouthguard fillers and whitening professional products, comprising the steps of:
   a) providing an aqueous suspension including particles according to claim 1; and
   b) mixing said aqueous suspension with other ingredients of the oral care and oral hygiene product.

16. A process for manufacturing an oral care and oral hygiene product having photocatalytic activity selected from the group consisting of: toothpaste, tooth powder, chewing gum, ointment for the gums, mouthwash and mouth bath concentrate, gargle, bite and mouthguard fillers and whitening professional products, comprising the steps of:
   a') providing solid particles according to claim 1; and
   b') mixing the solid particles with other ingredients of the oral care and oral hygiene product.

17. A process according to claim 15, wherein said step a) comprises the steps of:

$a_l$) preparing an aqueous solution comprising calcium ions at a concentration comprised between $10^{-4}$M and $10^{-2}$M, preferably $10^{-3}$M;

$b_1$) heating said aqueous solution to a temperature comprised between 30° and 120° C., preferably 80° C., for a time comprised between 0.5 and 4 hours until said temperature is reached;

$c_1$) adding drop-wise an aqueous solution containing phosphate ions at a concentration comprised between $0.5 \cdot 10^{-4}$ M and $0.5 \cdot 10^{-2}$ M, preferably $0.6 \cdot 10^{-3}$ M, over a time ranging between 2 h and 8 h, preferably 4 h;

$d_1$) adding drop-wise, simultaneously with the addition of the solution containing phosphate ions, an alcoholic solution of a titanium compound at a concentration comprised between $0.05 \cdot 10^{-4}$ M and $0.05 \cdot 10^{-2}$ M, preferably $0.05 \cdot 10^{-3}$ M;

$e_1$) refluxing the resulting mixture for a time comprised between 4 h and 12 h, preferably 8 h.

18. A process according to claim 17, wherein in step $d_1$), the alcohol used to make the alcohol solution is selected from the group comprising: methanol, ethanol, isopropanol, propanol, butanol, octanol and mixtures thereof.

19. A process according to claim 17, wherein in step $d_1$), the titanium compound used is selected from the group comprising: a titanium alkoxide, preferably titanium isopropoxide or titanium butoxide, and an inorganic precursor of titanium dioxide.

20. A process according to claim 17, wherein step $c_1$) is carried out by simultaneously agitating the solution, preferably by means of a mechanical stirrer, in order to capture the $CO_2$ present in the atmosphere, or by adding carbonate ions to the aqueous solution containing phosphate ions, or by simultaneously adding a first solution containing carbonate ions and a second solution containing phosphate ions.

21. A process according to claim 16, wherein said step a') comprises the steps of:

$a_3$) preparing an aqueous suspension including the particles according to step a);

$b_3$) separating the solid particles from the suspension obtained from step $a_3$);

$c_3$) drying the wet solid particles thus obtained.

22. A process according to claim 21, wherein said separation step $b_3$) is carried out by decantation, centrifugation or filtration.

23. A process according to claim 21, wherein said drying step $c_3$) is carried out by freeze-drying the wet solid particles at a temperature lower than 0° C. until reaching a constant weight.

24. A process according to claim 21, further comprising the step of:

$d_3$) washing the separated solid particles with water or a basic solution prior to effecting said drying step $c_3$).

25. A process according to claim 15, wherein mixing step b) is carried out in a mixing apparatus maintained under vacuum.

26. A process according to claim 15, wherein mixing step b) is carried out by $b^1$) mixing the aqueous suspension of step a) with other ingredients of the oral care and oral hygiene product except for any surfactant;

$b^2$) incorporating at least one surfactant into the mixture thus obtained.

27. A kit of parts comprising at least an oral care and oral hygiene product having photocatalytic activity according to claim 1 and optionally at least a light emitting device having a wavelength comprised between 280 nm and 450 nm.

28. A process according to claim 16, wherein mixing step b') is carried out in a mixing apparatus maintained under vacuum.

29. A product according to claim 3, wherein the $TiO_2$ nanoparticles have a length comprised between 0.01 μm and 0.1 μm.

* * * * *